United States Patent [19]
McCaffrey et al.

[11] Patent Number: 5,807,982
[45] Date of Patent: Sep. 15, 1998

[54] AFFINITY PURIFIED HEPARIN

[75] Inventors: Timothy A. McCaffrey, New York; Domenick J. Falcone, Flushing, both of N.Y.

[73] Assignee: Cornell Research Foundation, Inc., Ithaca, N.Y.

[21] Appl. No.: 692,921

[22] Filed: Apr. 29, 1991

[51] Int. Cl.⁶ .............................. A61K 38/00; C07K 5/00; C07K 7/00
[52] U.S. Cl. .............................. 530/328; 530/412; 536/21
[58] Field of Search ..................................... 530/328, 412; 536/21

[56] References Cited

U.S. PATENT DOCUMENTS 4,971,952  11/1990  Bentz et al. .............................. 514/12

OTHER PUBLICATIONS

Cheifetz et al., Cell, vol. 48, pp. 409–417, Feb. 13, 1987.
Andersson et al., Biological Abstracts, BA:3733, p. 357, Jan. 1, 1978.
Jozefonnicz et al., Chemical Abstracts, CA113(21): 187597s, 1990.

*Primary Examiner*—Avis M. Davenport
*Attorney, Agent, or Firm*—Nixon, Hargrave, Devans & Doyle LLP

[57] ABSTRACT

The present invention relates to a method for purifying heparin into two subspecies of molecules, one which binds transforming growth factor-β (TGF-β), and another which does not. The method involves using a peptide, immobilized on a chromatography substrate, that is homologous to the heparin-binding region of TGF-β and allowing the heparin to contact the immobilized peptide for a sufficient time to cause binding. The fraction of heparin which does not bind to the peptide retains its activity as an anticoagulant but is devoid of the ability to bind TGF-β.

12 Claims, 7 Drawing Sheets

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:1:

Ser  Lys  Lys  His  Ala  Glu  Lys  His  Trp  Phe
 1                    5                         1 0

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:2:

Gly  Leu  Lys  Lys  Asn  Gly  Arg  Ser  Lys  Leu
 1                    5                         1 0

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:3:

Pro  Lys  Arg  Leu  Tyr  Cys  Lys  Asn  Gly  Gly
 1                    5                         1 0

( 2 ) INFORMATION FOR SEQ ID NO:4:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( x i ) SEQUENCE DESCRIPTION: SEQ ID NO:4:

| Leu | Tyr | Arg | Lys | Ala | Ala | Lys | Ser | Ser | Lys |
|-----|-----|-----|-----|-----|-----|-----|-----|-----|-----|
| 1   |     |     |     | 5   |     |     |     |     | 10  |

( 2 ) INFORMATION FOR SEQ ID NO:5:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( x i ) SEQUENCE DESCRIPTION: SEQ ID NO:5:

| Leu | Phe | Arg | Lys | Leu | Thr | His | Arg | Leu | Phe |
|-----|-----|-----|-----|-----|-----|-----|-----|-----|-----|
| 1   |     |     |     | 5   |     |     |     |     | 10  |

( 2 ) INFORMATION FOR SEQ ID NO:6:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( x i ) SEQUENCE DESCRIPTION: SEQ ID NO:6:

| Asp | Phe | Arg | Lys | Asp | Leu | Gly | Trp | Lys | Trp |
|-----|-----|-----|-----|-----|-----|-----|-----|-----|-----|
| 1   |     |     |     | 5   |     |     |     |     | 10  |

( 2 ) INFORMATION FOR SEQ ID NO:7:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( x i ) SEQUENCE DESCRIPTION: SEQ ID NO:7:

| Met | Tyr | Lys | Lys | Phe | Lys | Leu | Leu |
|-----|-----|-----|-----|-----|-----|-----|-----|
| 1   |     |     |     | 5   |     |     |     |

( 2 ) INFORMATION FOR SEQ ID NO:8:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( x i ) SEQUENCE DESCRIPTION: SEQ ID NO:8:

| Phe | Val | Arg | Lys | Tyr | Arg | Ala | Ala |
|-----|-----|-----|-----|-----|-----|-----|-----|
| 1   |     |     |     | 5   |     |     |     |

( 2 ) INFORMATION FOR SEQ ID NO:9:

( i ) SEQUENCE CHARACTERISTICS:
( A ) LENGTH: 8 amino acids
( B ) TYPE: amino acid
( D ) TOPOLOGY: linear (i i) MOLECULE TYPE: peptide (x i) SEQUENCE DESCRIPTION: SEQ ID NO:9:

Glu Ala Leu Arg Ala Arg Met Glu
1               5

(2) INFORMATION FOR SEQ ID NO:10:

(i) SEQUENCE CHARACTERISTICS:
      (A) LENGTH: 8 amino acids
      (B) TYPE: amino acid
      (D) TOPOLOGY: linear    (i i) MOLECULE TYPE: peptide    (x i) SEQUENCE DESCRIPTION: SEQ ID NO:10:

Gln Arg His Lys Val Arg Glu Glu
1               5

(2) INFORMATION FOR SEQ ID NO:11:

(i) SEQUENCE CHARACTERISTICS:
      (A) LENGTH: 8 amino acids
      (B) TYPE: amino acid
      (D) TOPOLOGY: linear    (i i) MOLECULE TYPE: peptide    (x i) SEQUENCE DESCRIPTION: SEQ ID NO:11:

Val Gly Arg Lys Phe Lys Val Glu
1               5

(2) INFORMATION FOR SEQ ID NO:12:

(i) SEQUENCE CHARACTERISTICS:
      (A) LENGTH: 12 amino acids
      (B) TYPE: amino acid
      (D) TOPOLOGY: linear    (i i) MOLECULE TYPE: peptide    (x i) SEQUENCE DESCRIPTION: SEQ ID NO:12:

Gly Lys Gly Pro Arg Pro Phe His Cys Arg Gln Ile
1               5                   10

(2) INFORMATION FOR SEQ ID NO:13:

(i) SEQUENCE CHARACTERISTICS:
      (A) LENGTH: 12 amino acids
      (B) TYPE: amino acid
      (D) TOPOLOGY: linear    (i i) MOLECULE TYPE: peptide    (x i) SEQUENCE DESCRIPTION: SEQ ID NO:13:

Arg Lys Ala His Lys Ser Ser Lys Leu Val Ser Ala
1               5                   10

(2) INFORMATION FOR SEQ ID NO:14:

(i) SEQUENCE CHARACTERISTICS:
      (A) LENGTH: 12 amino acids
      (B) TYPE: amino acid
      (D) TOPOLOGY: linear    (i i) MOLECULE TYPE: peptide    (x i) SEQUENCE DESCRIPTION: SEQ ID NO:14:

-continued

```
Gln  Lys  Tyr  Thr  Lys  Tyr  Ser  Lys  His  Asp  Met  Asn
 1              5                        10
```

(2) INFORMATION FOR SEQ ID NO:15:

(i) SEQUENCE CHARACTERISTICS:
        (A) LENGTH: 12 amino acids
        (B) TYPE: amino acid
        (D) TOPOLOGY: linear     (ii) MOLECULE TYPE: peptide     (xi) SEQUENCE DESCRIPTION: SEQ ID NO:15:

```
Arg  Lys  Trp  Leu  Lys  Met  Phe  Lys  Lys  Arg  Gln  Leu
 1              5                        10
```

(2) INFORMATION FOR SEQ ID NO:16:

(i) SEQUENCE CHARACTERISTICS:
        (A) LENGTH: 12 amino acids
        (B) TYPE: amino acid
        (D) TOPOLOGY: linear     (ii) MOLECULE TYPE: peptide     (xi) SEQUENCE DESCRIPTION: SEQ ID NO:16:

```
Pro  Arg  Gly  Glu  Arg  Gly  Pro  Arg  Gly  Ile  Thr  Gly
 1              5                        10
```

(2) INFORMATION FOR SEQ ID NO:17:

(i) SEQUENCE CHARACTERISTICS:
        (A) LENGTH: 12 amino acids
        (B) TYPE: amino acid
        (D) TOPOLOGY: linear     (ii) MOLECULE TYPE: peptide     (xi) SEQUENCE DESCRIPTION: SEQ ID NO:17:

```
Trp  Lys  Trp  Ile  His  Glu  Pro  Lys  Gly  Tyr  His  Ala
 1              5                        10
```

(2) INFORMATION FOR SEQ ID NO:18:

(i) SEQUENCE CHARACTERISTICS:
        (A) LENGTH: 10 amino acids
        (B) TYPE: amino acid
        (D) TOPOLOGY: linear     (ii) MOLECULE TYPE: peptide     (xi) SEQUENCE DESCRIPTION: SEQ ID NO:18:

```
Asp  Phe  Arg  Lys  Asp  Ile  Gly  Trp  Lys  Trp
 1              5                        10
```

AFFINITY PURIFIED HEPARIN

Partial support for the making of the present invention was provided by the US government under National Institutes of Health Grant Nos. HL-35724, HL-01962, and HL-18828. Accordingly, the United States government has certain rights to the invention described and claimed herein.

Heparin is a recognized inhibitor of blood coagulantion. Heparin is a highly sulfated polysaccharide purified from the livers and lungs of domestic animals, especially porcine and bovine tissues. Heparin binds to the polypeptide antithrombin III (AT III) and greatly accelerates AT III's ability to inactivate the procoagulant enzyme thrombin in blood. Thus, heparin is widely used as an anticoagulant in the treatment of a broad range of thrombotic disorders.

Heparin is also an antiproliferative. Infusions of heparin following balloon-catheter (Fogarty) distension of the rat thoracic aorta blocks the subsequent neointimal hyperplasia due to the proliferation and migration of medial smooth muscle cells (SMC). In vitro, heparin inhibits the growth of SMCs, fibroblasts, and, in some cases, endothelial cells. Based upon this antiproliferative activity, heparin has been proposed both as an antiatherosclerotic agent and as a therapeutic agent to block the occlusive proliferation of SMC that follows percutaneous transluminal angioplasty (PCTA). However, long-term heparin use is associated with serious side effects including osteoporosis and thrombocytopenia. As many as half of patients receiving heparin for a period over 6 months develop clinically significant osteoporosis. Essentially all patients treated with heparin exhibit a transient thrombocytopenia, and approximately 5% of those patients persist in that state for the duration of therapy. These two side effects of heparin significantly limit the clinical use of this important anticoagulant, particularly for long term use. The biological basis for these side effects is unknown.

We have now discovered that heparin, in addition to binding to AT III and other proteins, binds to transforming growth factor-$\beta$ (TGF-$\beta$). When binding to TGF-$\beta$, heparin prevents TGF-$\beta$ from being sequestered by alpha-2-macroglobulin, a component found in both plasma and tissues. This suggests that heparin changes the three-dimensional structure of TGF-$\beta$ or occupies amino acid groups necessary for binding TGF-$\beta$ to alpha-2-macroglobulin.

TGF-$\beta$ is also important to bone integrity. Bone is a major reservoir of TGF-$\beta$. When TGF-$\beta$ is injected into the fetal rat calvaria, new bone synthesis is dramatically increased. TGF-$\beta$ has profound effects on the growth and function of osteoclasts and osteoblasts, cells localized within bone that regulate bone integrity. Heparin may deplete bone of TGF-$\beta$. Based upon its ability to bind heparin and heparan sulfate, TGF-$\beta$ would be expected to bind cellular heparan sulfate proteoglycans in bone. Heparin in the bloodstream would compete with these endogenous binding sites for TGF-$\beta$ binding, and as a result bone might become depleted of TGF-$\beta$ and thereby fail to produce the important matrix constituents that impart bone strength. The result of this bone weakening could lead to osteoporosis.

TGF-$\beta$ also regulates endothelial cell function and is known to influence the growth and metabolism of endothelial cells which line the arterial wall. TGF-$\beta$ inhibits endothelial cell growth and causes endothelial cells to express adhesion molecules. Because heparin may increase the circulating concentrations of active TGF-$\beta$, it may adversely influence endothelial cell-mediated platelet destruction, the result of which would be thrombocytopenia.

Accordingly, one aspect of the present invention describes a means of separating the anticoagulant activity of heparin from its ability to bind TGF-$\beta$. By utilizing a novel heparin preparation which does not bind TGF-$\beta$, we have developed a heparin which may have fewer side effects than the commercially available heparin presently being manufactured and sold for medical use.

This and other aspects of the present invention will become more apparent by reference to the following examples and figures which are presented to offer the reader a more thorough and complete understanding of the invention. These examples and figures are presented by way of illustration only and are not intended, nor should they be considered, to limit the scope of the claimed invention in any manner.

With specific reference to the figures,

FIG. 3 A and FIG. 3 B depict chromatographic elutions indicating the A1A regions of TGF-$\beta$ is capable of binding with heparin;

FIG. 4 A and FIG. 4 B depict chromatographic elutions indicating that the A2A region of TGF-$\beta$ binds heparin;

Figure 6:
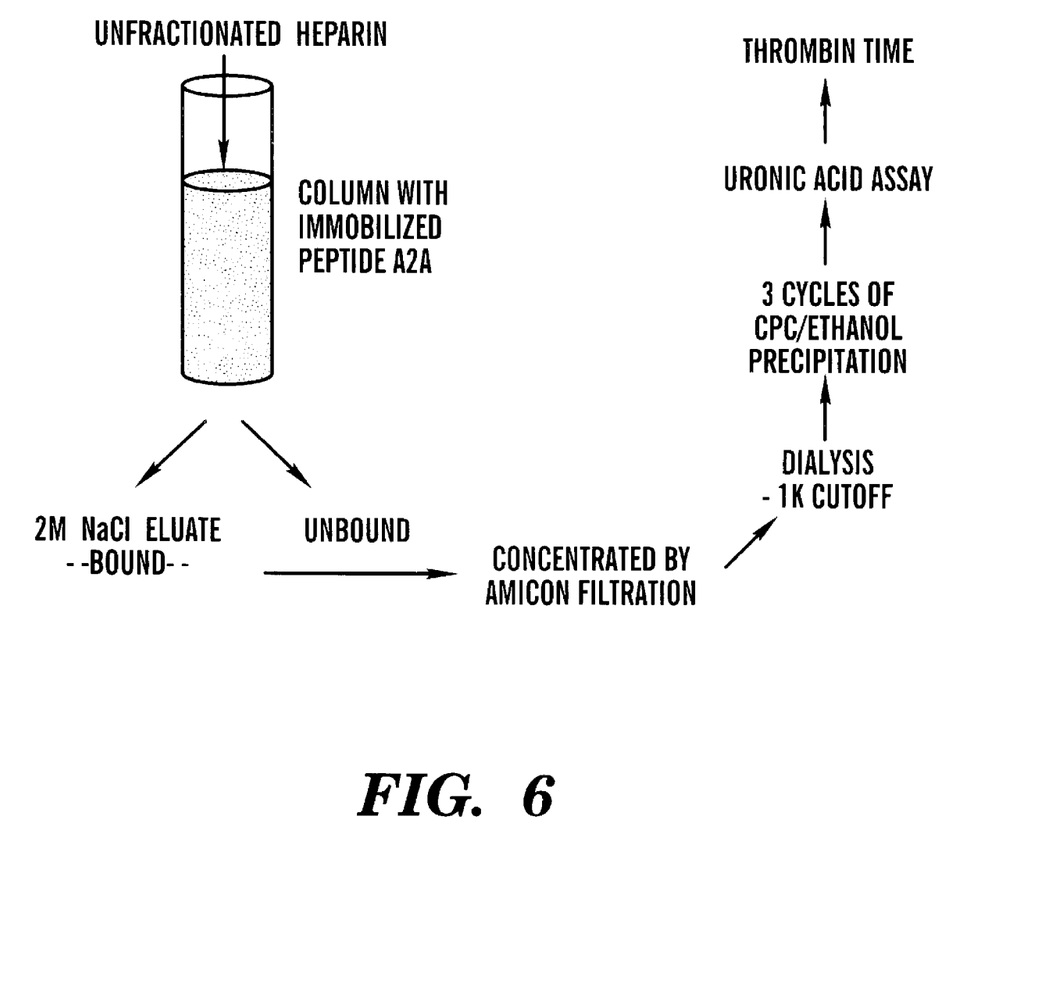
FIG. 6 depicts the flow scheme strategy for the isolation of the heparin purified against the heparin-binding region of TGF-$\beta$.

Throughout the following description reference will be made to heparin purification protocol for determining whether heparin was or was not bound by the immobilized peptide regions of TGF-$\beta$. This protocol is generally represented in FIG. 6, in which a column bearing immobilized peptide was loaded with heparin, and the unbound fraction collected. Any bound heparin was then washed or eluted from the column with 2M NaCl, the unbound heparin was applied again to the column, and the unbound fraction retained. The bound fraction was then eluted with 2M NaCl and pooled with the first bound fraction. The heparins were then concentrated by ultrafiltration utilizing an Amicon filter, dialysed to remove the salt, and precipitated with cetylpyridinium chloride. The precipitate was next dissolved in water and precipitated 3 times with ethanol to remove the cetylpyridinium chloride. The purified heparins would then be assayed for uronic acid content and for their ability to prolong the thrombin clot time.

EXAMPLE I

These experiments document that purified TGF-$\beta$ has a particular affinity for heparin. More specifically, FIG. 1A demonstrates that iodinated ($^{125}$I) TGF-$\beta$ is a heparin-binding protein. TGF-$\beta$ (Type 1 from human or porcine platelets) was purchased from R&D Systems (Minneapolis, Minn.); TGF-$\beta$ was iodinated by known chloramine T methods to a specific activity of 1.5 to 2.5×10$^6$ cpm/ng protein. Heparin-sepharose was purchased from Pharmacia Inc. and contained in an 2.5×16 cm glass column. Unless otherwise described, all column reagents, including salts, for the binding and elution of column ligands were suspended in 5 mM Tris-acetate buffer (pH 7.0).

Figure 1A:
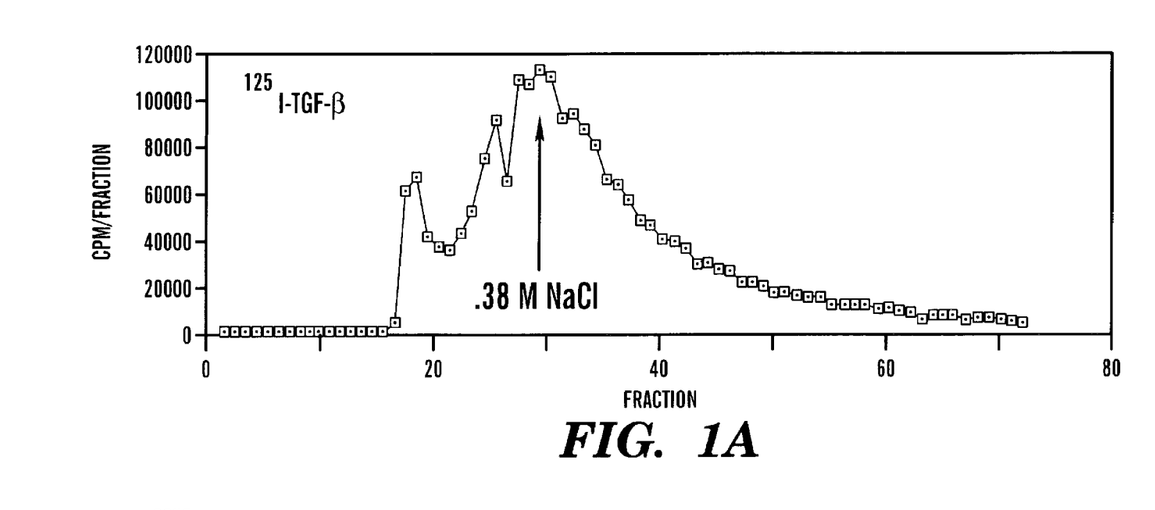
FIG. 1A and 1B depict that radiolabelled TGF-$\beta$ is a heparin-binding protein.
Figure 1B:
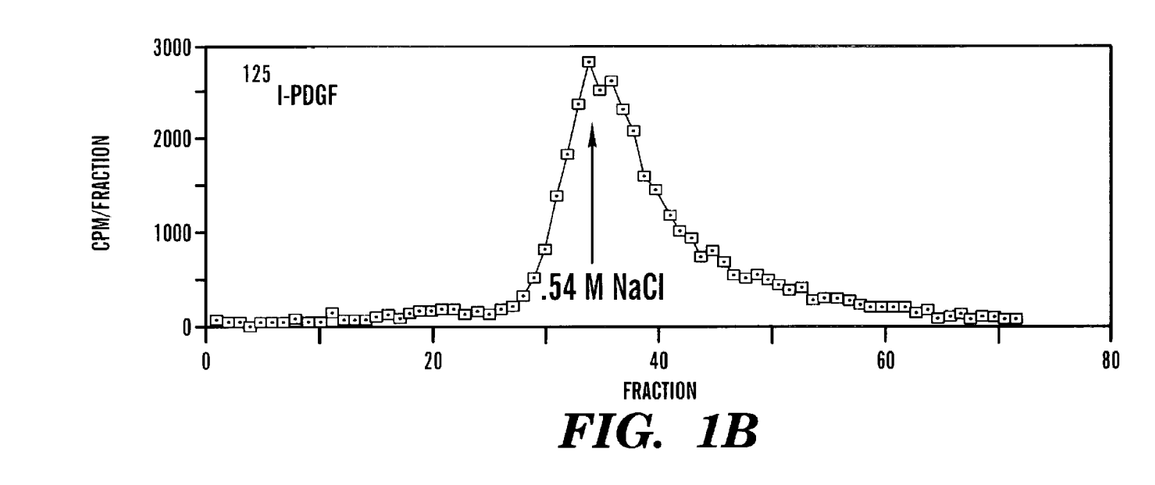

Iodinated TGF-β was applied to a heparin-sepharose column followed by a thorough washing with 5 mM Tris-acetate, pH 7.0, buffer. Beginning with fraction 0 (depicted on the "X" axis), a gradient of buffer containing an increasing amount of NaCl (0–2M) was applied and 2–3 ml fractions were collected and counted in a gamma counter. The results indicate that the radiolabelled TGF-β was eluted from the heparin-sepharose with 0.38M NaCl. For comparison purposes, the same procedure was repeated (the results are depicted in FIG. 1B) with radiolabelled PDGF, a well-known heparin-binding protein. The results in FIG. 1B confirms previously published data indicating that PDGF elutes from heparin-sepharose with 0.54M NaCl. Thus, this data clearly confirms that radiolabelled TGF-β is capable of binding to immobilized heparin.

EXAMPLE II

Figure 2:
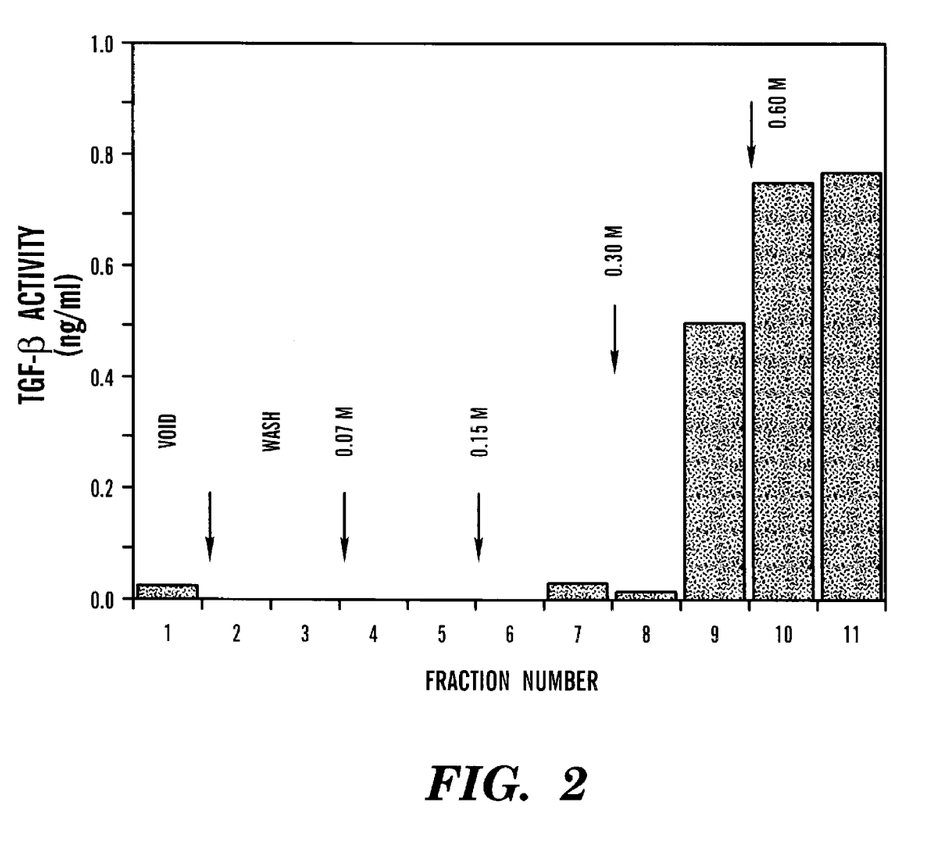
FIG. 2 depicts data of a confirmatory test to show TGF-$\beta$ is a heparin-binding protein.

In order to eliminate the possibility that TGF-β only binds to heparin when the TGF-β is iodinated, a similar set of experiments were performed using native, unlabelled TGF-β. A known amount (100 ng) of TGF-β was applied to a smaller heparin-sepharose column, washed twice with 0.5 ml of 0.5 mM TRIS-acetate buffer, and then the same volumes of buffer with increasing salt concentration (shown in FIG. 2) were applied. Fractions were collected and 5 μl samples were tested for TGF-β activity in a standard CCL64 cell inhibition assay. The fractions were also tested for conductance to determine the salt concentration in the samples. The results indicate that, like radiolabelled TGF-β, the native protein eluted from the heparin-sepharose column with greater than 0.3M NaCl. Only 1.5% of the activity was not retained (void) by the column. This confirms that TGF-β is a heparin-binding protein.

In order to purify heparin subspecies which have high or low affinity, either the native TGF-β protein or a peptide homologous to TGF-β's heparin-binding region could be used. Since the native protein is costly and prone to proteolysis, the possible heparin-binding regions of the protein were identified by virtue of the placement of the basic residues. As shown in the following table, several regions of the TGF-β molecule were tested for their ability to bind heparin. The location of the basic amino acids in TGF-β was identified from the published human TGF-β sequence, and it was found that a high percentage of these basic residues thought to mediate heparin binding fell within a 20 amino acid region of the TGF-β molecule. Synthetic peptides homologous to these regions, or to unrelated regions as controls, were then prepared, and the heparin-binding ability of these peptides was analyzed by conventional heparin-Sepharose chromatography. These peptides were purchased from BioSynthesis Inc. (Denton, Tex.).

Certain patterns of basic amino acids such as lysine, arginine, and histidine have previously been identified as possible or confirmed heparin-binding regions within other proteins. These motifs, wherein "B" represents a basic moiety, are depicted in the following Table I which list three possible heparin-binding motifs and examples of amino acid sequences of heparin-binding proteins. In each of the three cases, a similar region within TGF-β was identified. Synthetic peptides homologous to each of the three regions were prepared by conventional techniques and designated by A1A, A2A, and A4A.

TABLE I

| | | | | | | | | | | | |
|---|---|---|---|---|---|---|---|---|---|---|---|
| TYPE 1 HEPARIN-BINDING SITE: | | | | | | | | | | | |
| MOTIF | | — | B | B | B | — | — | B | — | — | — |
| aFGF(Seq 1) | 99 | Ser | Lys | Lys | His | Ala | Glu | Lys | His | Trp | Phe |
| bFGF(Seq 2) | 110 | Gly | Leu | Lys | Lys | Asn | Gly | Arg | Ser | Lys | Leu |
| (Seq 3) | 20 | Pro | Lys | Arg | Leu | Tyr | Cys | Lys | Asn | Gly | Gly |
| AT III(Seq 4) | 130 | Leu | Tyr | Arg | Lys | Ala | Ala | Lys | Ser | Ser | Lys |
| HepCo II (Seq 5) | 182 | Leu | Phe | Arg | Lys | Leu | Thr | His | Arg | Leu | Phe |
| A2A(Seq 6) | 25 | Asp | Phe | Arg | Lys | Asp | Leu | Gly | Trp | Lys | Trp |
| TYPE 2 HEPARIN-BINDING SITE: | | | | | | | | | | | |
| MOTIF | | — | — | B | B | — | B | — | — | | |
| aFGF(Seq 7) | 7 | Met | Tyr | Lys | Lys | Phe | Lys | Leu | Leu | | |
| Apo B(Seq 8) | 2080 | Phe | Val | Arg | Lys | Tyr | Arg | Ala | Ala | | |
| Apo E(Seq 9) | 212 | Glu | Ala | Leu | Arg | Ala | Arg | Met | Glu | | |
| FN(Seq 10) | 2148 | Gln | Arg | His | Lys | Val | Arg | Glu | Glu | | |
| A4A(Seq 11) | 92 | Val | Gly | Arg | Lys | Phe | Lys | Val | Glu | | |
| TYPE 3 HEPARIN-BINDING SITE: | | | | | | | | | | | |
| MOTIF | | — | B | — | — | B | — | — | B | — | — | B | — |
| HRGP(Seq 12) | 462 | Gly | Lys | Gly | Pro | Arg | Pro | Phe | His | Cys | Arg | Gln | Ile |
| ATIII(Seq 13) | 132 | Arg | Lys | Ala | His | Lys | Ser | Ser | Lys | Leu | Val | Ser | Ala |
| LPC(Seq 14) | 238 | Gln | Lys | Tyr | Thr | Lys | Tyr | Ser | Lys | His | Asp | Met | Asn |
| PCI(Seq 15) | 270 | Arg | Lys | Trp | Leu | Lys | Met | Phe | Lys | Lys | Arg | Gln | Leu |
| Coll(Seq 16) | V361 | Pro | Arg | Gly | Glu | Arg | Gly | Pro | Arg | Gly | Ile | Thr | Gly |
| A1A(Seq 17) | 30 | Trp | Lys | Trp | Ile | His | Glu | Pro | Lys | Gly | Try | His | Ala |

In the preceeding tables, aFGF is acidic fibroblast growth factor; bFGF is basic FGF; AT III is antithrombin III; HepCo II is heparin cofactor II; A2A is a region of TGF-β; Apo B is apolipoprotein B; FN is fibronectin; A4A is a region of TGF-β; HRGP is histidine-rich glycoprotein; LPC is lipocortin; PCI is protein C inhibitor; Coll V is Type V Collagen; and A1A is a region of TGF-β.

Figure 3A:
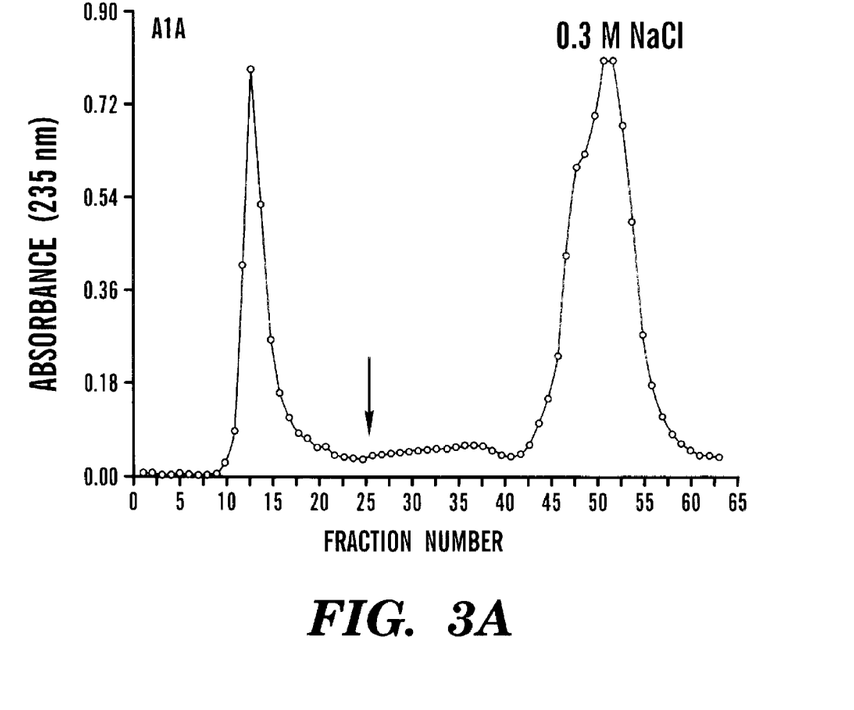

In order to determine whether the predicted heparin-binding regions were actually capable of binding heparin, 1 ml of 3–5 mg/ml solution of the peptide was applied to a heparin-sepharose column as described in Example I. The elution of the peptide was monitored by its absorbance at 235 or 247 nM. Unlike native TGF-β, which was almost fully retained by the column, a substantial fraction of the peptides eluted from the column in NaCl-free buffer. After beginning the NaCl gradient (depicted at the arrow in FIG.

Figure 3B:
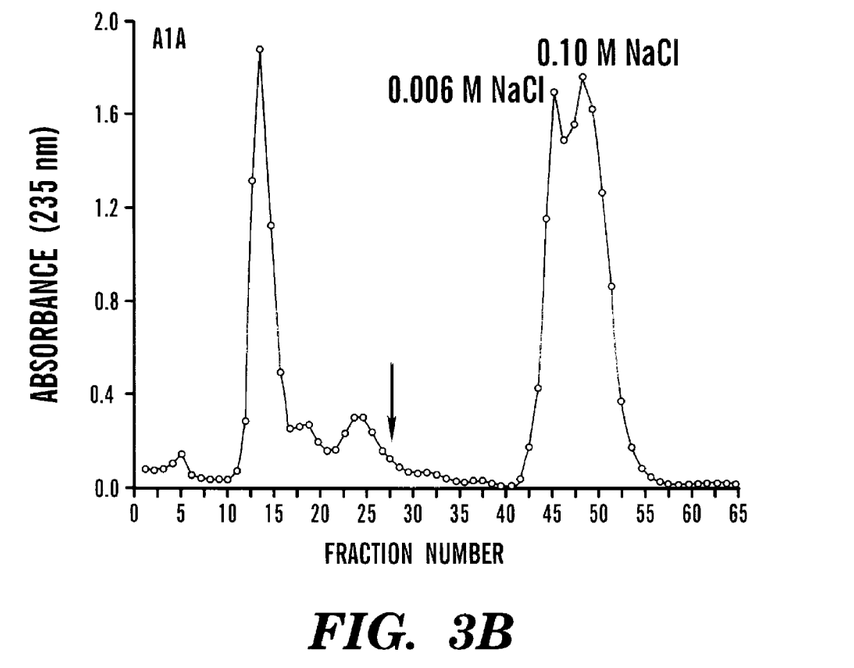

3A), it was observed that the majority of the peptide was retained and eluted at the salt concentration specified. With the column equilibrated in 5 mM TRIS-acetate buffer, the peptide A1A eluted with 0.3M NaCl (FIG. 3A). With the column equilibrated in 5M urea, peptide A1A eluted between 0.006 and 0.1M NaCl, well below physiological salt concentration (FIG. 3B). This indicates that in its native state, but not in its urea-denatured state, this region of the molecule would be expected to bind heparin.

Figure 4A:
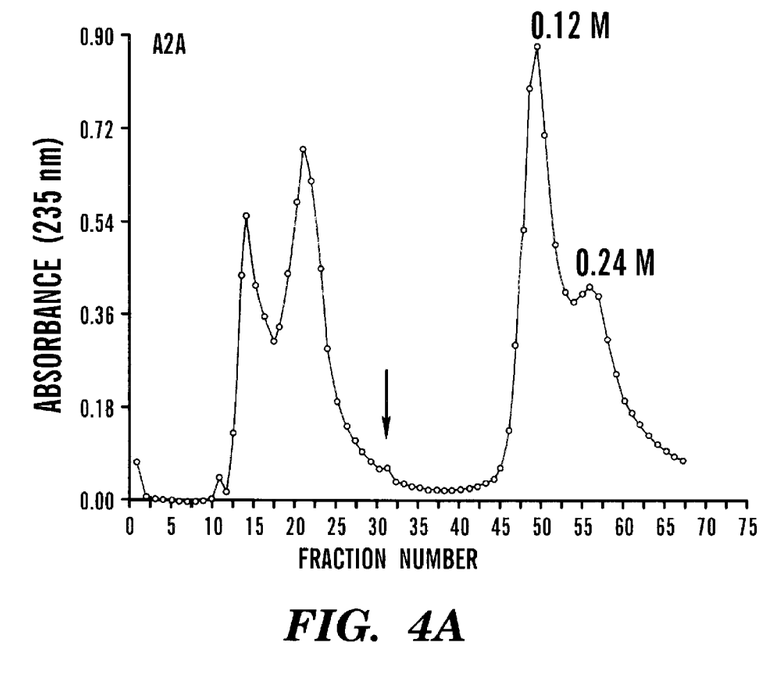
Figure 4B:
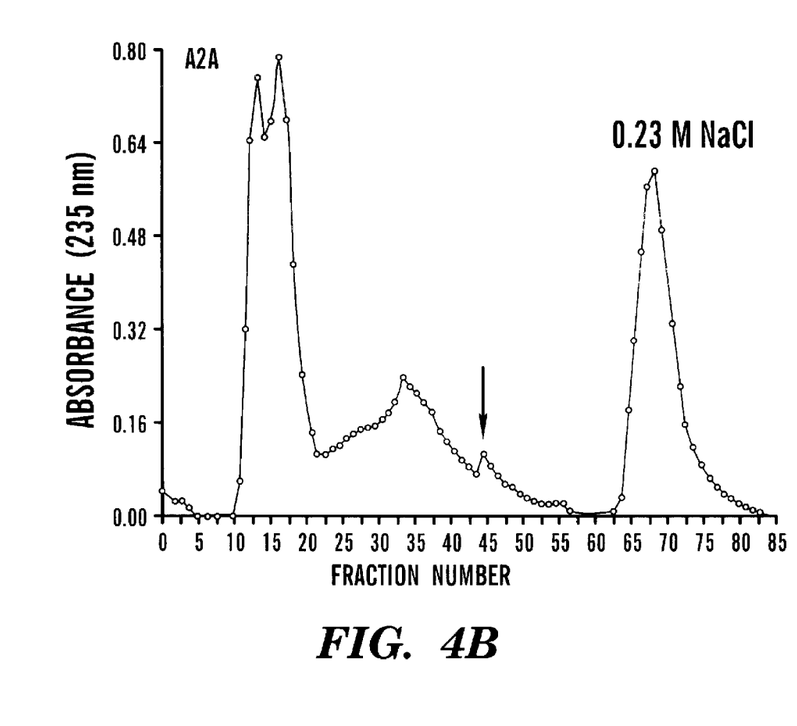

The protocol used to obtain the elution described in FIG. 3 was repeated using peptide A2A. As shown in FIG. 4, when peptide A2A was applied to the heparin-sepharose column, a substantial non-binding fraction was observed in fractions 15–20. As the NaCl gradient began (at the arrow), A2A eluted at 0.12 to 0.24M NaCl under native conditions (FIG. 4A). In 5M urea (FIG. 4 B), A2A eluted at 0.23M NaCl, suggesting that the peptide assumes a tertiary structure of inter- and intra-molecular bonds that reduces its heparin binding ability in its native configuration. Thus, this site may be a physiologically important site in the native molecule where its tertiary structure would be defined by adjacent and distal protein structures.

Figure 5A:
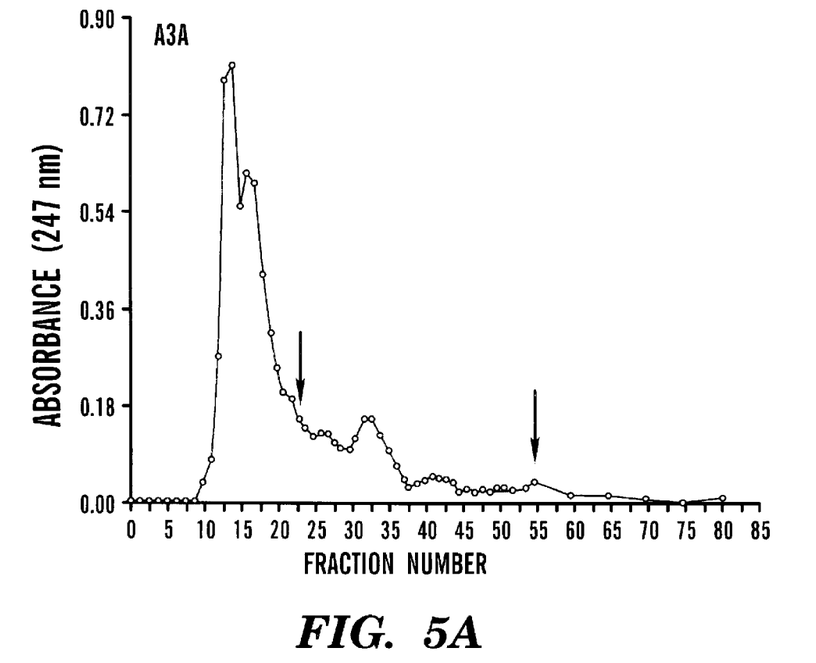
FIG. 5A and FIG. 5B depicts that the heparin-binding ability of peptides A1A and A2A are specific TGF-$\beta$ binding regions and not a property of the A3A region.
Figure 5B:
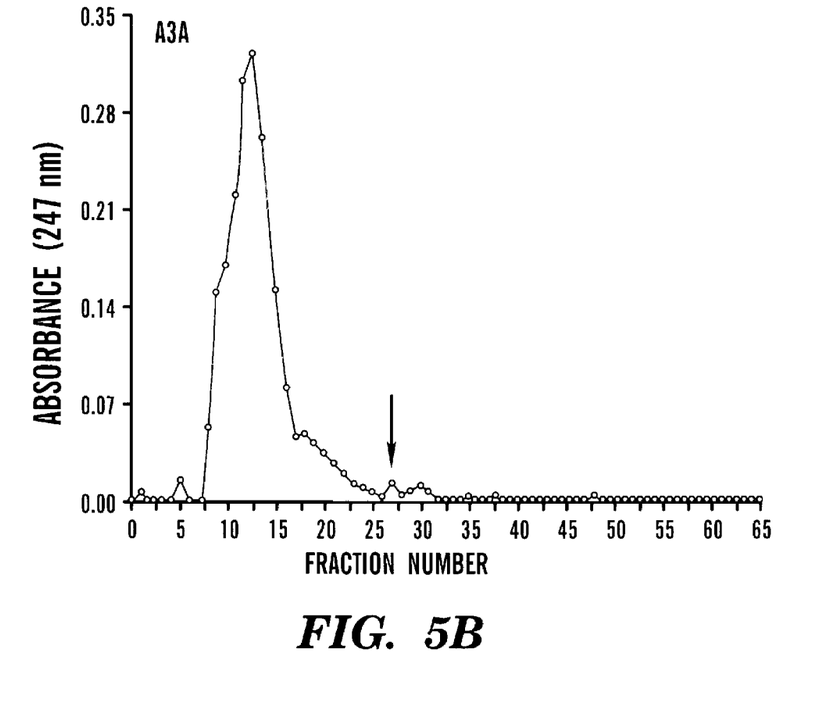

Once again the protocols used above were maintained. The A3A peptide depicted in FIG. 5 was derived from a third region of TGF-β that does not exhibit the typical characteristics of a heparin-binding region. Its sequence begins with the amino acid 49 of the mature 26 kD TGF-β protein and reads: —Pro Tyr Ile Trp Ser Ile Asp Thr Gln Tyr—. It was used in the protocol to determine whether any peptide of this size would bind to heparin-sepharose. As shown in FIG. 5A (native) and 5B (5M urea denatured), the A3A peptide completely voided from the column and no additional peptide was eluted with NaCl. Likewise, peptide A4A, shown in Table 1, was fully retained by heparin-Sepharose, but eluted with physiological salt concentrations (0.15M NaCl), indicating it probably would not be active in vivo. Thus, this indicates that the heparin-binding ability of peptides A1A and A2A are specific for these regions of TGF-β and not any portion of the molecule.

To reiterate, the synthetic peptides containing basic residues were found to exhibit heparin binding properties. Peptide A1A was retained by heparin-sepharose with 0.3M NaCl affinity (FIG. 3A). Peptide A2A bound less strongly, and was eluted with two peaks of 0.12M and 0.24M NaCl (FIG. 4A). Peptide A3A was not retained by heparin-Sepharose (FIG. 5A) and peptide A4A bound, but was released by physiological salt concentrations. All peptides contained a fraction that failed to bind upon reapplication to the column suggesting the existence of a certain modified or degraded subspecies in the peptide preparations.

To eliminate tertiary structures of the peptides that might stearically hinder binding of peptides to heparin-sepharose, peptide separation was repeated on a column equilibrated with a powerful denaturant, 5M urea (pH 7.0). This disruption in tertiary structure, particularly in alpha-helical structure, dramatically reduced the affinity of the A1A peptide (FIG. 3B), suggesting that its secondary and tertiary structure is important to its heparin-binding ability. Conversely, the presence (FIG. 4A) of 5M urea increased the affinity of A2A to greater than 0.2M NaCl (FIG. 4B), suggesting that tertiary constraints blocked its 3 sequential basic residues. The failure of the A3A peptide to bind heparin was unchanged in the presence of urea (FIG. 5B). Thus, the present invention has been successful to identify two distinct heparin-binding regions within the TGF-β molecule.

These heparin-binding regions were then used to determine whether a commercial heterogeneous heparin preparation could be depleted of the ability to bind TGF-β since the depleted fraction, voided by a peptide column, might have different biological actions. This is described in the following example.

EXAMPLE III

Heparin was depleted of its ability to bind TGF-β by the following technique: Based upon amino acid sequence homology with other known heparin-binding proteins as described in Example 3, a synthetic peptide designated A2A was created which contained a heparin-binding region of TGF-β. This peptide was then immobilized on activated agarose by known Amino-link (Pierce Chemicals) methodology. A column of approximately 2 mls volume was observed to retain 14 mg of the peptide A2A. One milligram of heparin was dissolved in 1 ml of 50 mM TRIS-acetate pH 7.0 (TRIS), applied to the column, and allowed to incubate for 2 hours. The unbound fraction was collected with 3 column volumes of TRIS. The bound fraction was collected by a washing with 3 column volumes of 2M NaCl. The unbound fraction was reapplied to the washed column, reincubated and recollected as before. The resulting bound fraction on the column was eluted with 2M NaCl as before, and pooled with the first bound fraction. The two heparin fractions (bound and unbound) were purified using conventional techniques. The heparin samples were dialysed against water to remove excess salts, precipitated with cetylpyridium chloride (1.8% final concentration), and purified by 3 rounds of ethanol (>95%) precipitation to remove excess cetylpyridium chloride.

The amount of heparin bound or not bound by the peptide was then assessed by determining the uronic acid acid content of the fractions utilizing the method of Blumenkrantz and Asboe-Hansen. After purification, a total of 670 ugs were recovered (67%). Of this amount, 648 ugs were in the bound fraction and 22.3 ugs were in the unbound fraction (2.23% effective yield). This low yield is due to extremely low ionic strength of the column buffer which can easily be adjusted to near physiological salt conditions to increase the yield of the unbound fraction.

Heparin was also assayed for its anticoagulant activity by conventional thrombin time assay. The bound, unbound, and unfractionated heparins were diluted until the thrombin-stimulated coagulation of whole human citrated plasma was prolonged from 10 seconds to 20 seconds. When compared to dilutions of known amounts of the original heparin, the concentrations of the heparin computed were identical to those observed in the uronic acid assay, indicating that the anticoagulant activity was unchanged by the purification procedure. Thus, the unbound fraction, which failed to bind the A2A peptide, was still capable of binding AT III and exerting anticoagulant activity.

EXAMPLE IV

Figure 7:
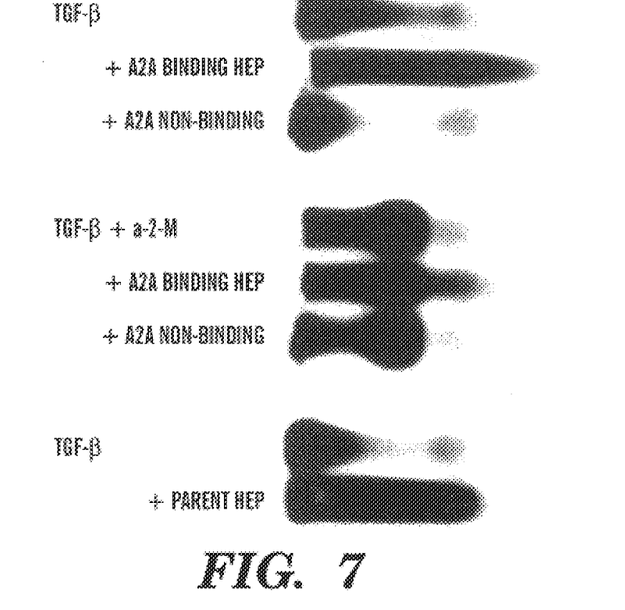
FIG. 7 is an autoradiogram produced from materials according to the present invention.

The heparin fractions were then assayed for their ability to bind native iodinated TGF-β by a previously published method (McCaffrey et al. J. Cell Biol. vol. 109, p. 441, 1989) As depicted in FIG. 7, heparin which bound the peptide A2A also bound authentic TGF-β as indicated by the anodic shift of the radiolabelled TGF-β on the autoradiogram. However, the unbound fraction, at equal concentrations, failed to bind TGF-β. This relationship was unchanged in the presence of alpha-2-macroglobulin, as shown in the middle 3 lanes. Therefore, this independent finding clearly establishes that the A2A peptide contains the heparin-binding region of TGF-β and that all heparin species which bind TGF-β have been removed by the A2A peptide affinity purification.

In order to determine whether this purification of heparin was specific for this peptide fragment, an identical purification with peptide A1A conducted as well as with a column devoid of peptide. Conditions were identical to those in Example 3. The stringency of the binding and wash buffers was increased to 50 mM NaCl and 50 mM TRIS pH 7.0. Alternatively, an identical column was prepared on which no peptide was immobilized (sham).

Figure 8:
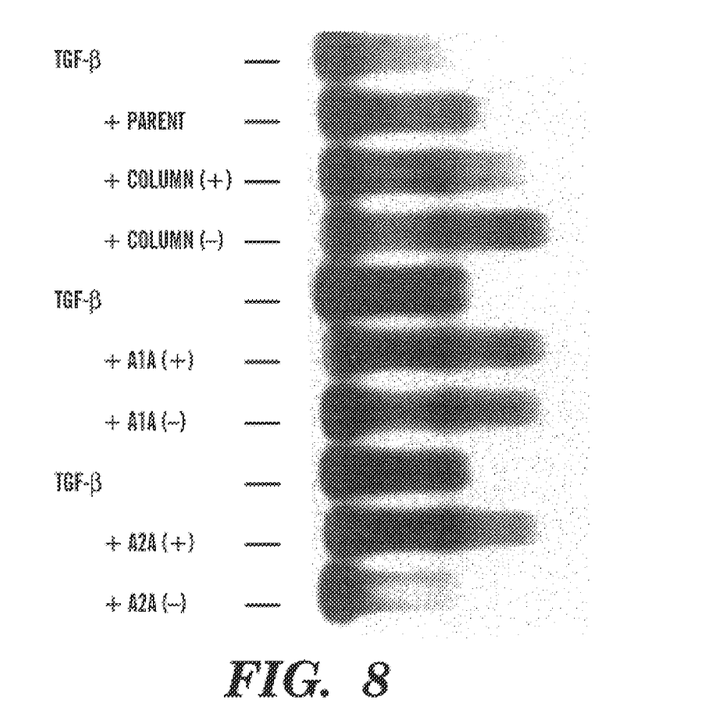
FIG. 8 is an autoradiogram produced to insure that FIG. 7 was not a chance occurrence.

After completion of the elution study, the sham column yielded fractions (4.5% bound, 34.1% unbound) that were still able to bind TGF-β. The peptide A1A bound 44.2% of the loaded heparin, though to a lesser degree than the A2A peptide which bound 66.6% of the loaded heparin. The resulting A1A unbound (FIG. 8, column+=Bound, column−=Unbound) fraction of heparin still was capable of binding authentic TGF-β. In contrast, the A2A peptide column produced heparin fractions (66.6% bound, 2.1% unbound) which had dramatically different abilities to bind authentic TGF-β. The A2A unbound heparin fraction had no apparent ability to bind authentic TGF-β. These results are shown in FIG. 8, and further support the belief that the A2A peptide contains the heparin-binding region of TGF-β.

Thus, while we have illustrated and described the preferred embodiments of our invention, it is to be understood that this invention is capable of variation and modification, and we therefore do not wish to be limited to the precise terms set forth, but desire to avail ourselves of such changes and alterations which may be made for adapting the invention to various usages and conditions. For example, other anion-exchanging substrates such as aminoethyl, diethylaminoethyl (DEAE), or quaternary aminoethyl, or synthetic analogues of this peptide region may be employed to fractionate heparin with respect to its TGF-β binding ability. Accordingly, such changes and alterations are properly intended to be within the full range of equivalents, and therefore within the purview, of the following claims.

Having thus described our invention and the manner and process of making and using it, in such full, clear, concise and exact terms so as to enable any person skilled in the art to which it pertains, or with which it is most nearly connected, and to make and use the same.

We claim:

1. A method for depleting heparin of a heparin subspecies with high or low affinity for transforming growth factor-beta which comprises:
    providing a polypeptide containing a heparin-binding region of TGF-β;
    immobilizing the polypeptide on an insoluble substrate;
    contacting the immobilized polypeptide with heparin for a sufficient time to allow binding; and
    collecting the unbound heparin.

2. A method according to claim 1 which further comprises purifying the bound heparin.

3. A method according to claim 1 which further comprises purifying the unbound heparin.

4. A method according to claim 1 wherein the polypeptide is transforming growth factor-beta, of natural or recombinant origin.

5. A method according to claim 1 wherein the polypeptide is of natural, recombinant or synthetic origin and contains the amino acid sequence:

Asp Phe Arg Lys Asp Leu Gly Trp (Seq 6) Lys Trp or a homologous structure with similar functionality thereof.

6. A purified Heparin subspecies having anticoagulant activity and which does not bind to transforming growth factor β.

7. A method according to claim 1 which further comprises collecting the bound heparin.

8. A method for purifying heparin fractions with high or low affinity for transforming growth factor-beta which comprises:

provi­ding a polypeptide containing a heparin-binding region of TGF-β;

immobilizing the polypeptide on an insoluble substrate;

contacting the immobilized polypeptide with heparin for a sufficient time to allow binding;

collecting the unbound fraction;

collecting the bound fraction; and concentrating the bound and unbound fractions.

9. A method according to claim 8 which further comprises collecting the bound fraction with 2M NaCl.

10. A method according to claim 8 which further comprises concentrating the bound and unbound fractions by dialysis and cetylpyridium chloride/ethanol precipitation.

11. A method according to claim 8 wherein the polypeptide is transforming growth factor beta of natural or recombinant origin.

12. A method according to claim 11 wherein the polypeptide contains the amino acid sequence:

Asp Phe Arg Lys Asp Leu Gly Trp Lys Trp (Seq. 6)

or a homologous structure with similar functionality.

* * * * *